US00PP18136P2

(12) United States Plant Patent
Dekker

(10) Patent No.: US PP18,136 P2
(45) Date of Patent: Oct. 23, 2007

(54) ***CHRYSANTHEMUM* PLANT NAMED 'MONA LISA YELLOW'**

(50) Latin Name: *Chrysanthemum×morifolium*
Varietal Denomination: Mona Lisa Yellow

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 11/417,364

(22) Filed: May 3, 2006

(51) Int. Cl.
*A01H 5/00* (2006.01)

(52) U.S. Cl. ..... Plt./289; Plt./287

(58) Field of Classification Search ..... Plt./287, Plt./289

See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Chrysanthemum* plant named 'Mona Lisa Yellow', characterized by its decorative anemone-type inflorescences with elliptic-shaped, light yellow-colored ray florets and darker yellow-colored enlarged disc florets; strong and upright flowering stems; freely flowering habit; early and uniform flowering response; and good postproduction longevity.

1 Drawing Sheet

Botanical designation: *Chrysanthemum×morifolium.*
Cultivar denomination: 'Mona Lisa Yellow'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Mona Lisa Yellow'.

The new *Chrysanthemum* is a naturally-occurring whole plant mutation of the *Chrysanthemum×morifolium* cultivar Mona Lisa Cream, disclosed in U.S. Plant patent application Ser. No. 11/267,907. The new *Chrysanthemum* was discovered and selected by the Inventor as a single flowering plant within a population of plants of the cultivar in May, 2004, in Hensbroek, The Netherlands. The selection of this plant was based on its attractive ray floret color and good inflorescence form.

Asexual reproduction of the new *Chrysanthemum* by terminal cuttings in a controlled environment in Hensbroek, The Netherlands since July, 2004, has shown that the unique features of this new *Chrysanthemum* are stable and reproduced true to type in successive generations.

SUMMARY OF THE INVENTION

Plants of the cultivar 'Mona Lisa Yellow' have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Mona Lisa Yellow'. These characteristics in combination distinguish 'Mona Lisa Yellow' as a new and distinct cultivar of *Chrysanthemum:*

1. Decorative anemone-type inflorescences with elliptic-shaped, light yellow-colored ray florets and darker yellow-colored enlarged disc florets; typically grown as a spray-type.
2. Strong and upright flowering stems.
3. Freely flowering habit.
4. Early and uniform flowering response; plants flower about seven weeks after the start of photoinductive treatments.
5. Good postproduction longevity; plants maintain good substance for about three weeks in an interior environment.

Plants of the new *Chrysanthemum* differ from plants of the parent, the cultivar Mona Lisa Cream, in the following characteristics:

1. Plants of the new *Chrysanthemum* have slightly darker green-colored leaves than plants of the cultivar Mona Lisa Cream.
2. Plants of the new *Chrysanthemum* are not as freely flowering as plants of the cultivar Mona Lisa Cream.
3. Plants of the new *Chrysanthemum* and the cultivar Mona Lisa Cream differ in ray floret color as plants of the cultivar Mona Lisa Cream have white-colored ray florets.

Plants of the new *Chrysanthemum* can be compared to plants of the *Chrysanthemum* cultivar Dekdakar, disclosed in U.S. Plant Pat. No. 16,009. In side-by-side comparisons conducted in Hensbroek, The Netherlands, plants of the new *Chrysanthemum* differed from plants of the cultivar Dekdakar in the following characteristics:

1. Plants of the new *Chrysanthemum* were stronger than plants of the cultivar *Dekdakar.*
2. Plants of the new *Chrysanthemum* had larger leaves than plants of the cultivar Dekdakar.
3. Plants of the new *Chrysanthemum* had larger inflorescences than plants of the cultivar Dekdakar.

BRIEF DESCRIPTION OF THE PHOTOGRAPHS

The accompanying colored photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Mona Lisa Yellow' grown as a natural spray.

The photograph at the bottom of the sheet is a close-up view of a typical flowering stem of 'Mona Lisa Yellow'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about eleven weeks from planting when the photographs and the description were taken.

Botanical classification: *Chrysanthemum×morifolium* cultivar 'Mona Lisa Yellow'.

Parentage: Naturally-occurring whole plant mutation of the *Chrysanthemum×morifolium* cultivar Mona Lisa Cream, disclosed in U.S. Plant patent application Ser. No. 11/267,907.

Propagation:

*Type.*—Terminal vegetative cuttings.

*Time to initiate roots.*—About six to seven days with temperatures about 20° C.

*Time to produce a rooted young plant.*—About 14 to 16 days with temperatures about 20° C.

*Root description/habit.*—Fine; light brown in color; freely branching.

Plant description:

*Appearance.*—Herbaceous decorative anemone-type cut flower that is typically grown as a natural spray.

*Flowering stem description.*—Aspect: Erect. Length: About 75 cm. Diameter: About 6 mm. Texture: Pubescent; longitudinally ridged. Color: 146A.

*Foliage description.*—Arrangement: Alternate; simple. Length: About 8 cm to 13 cm. Width: About 5 cm to 7.5 cm. Apex: Apiculate. Base: Attenuate. Margin: Palmately lobed. Texture, upper and lower surfaces: Pubescent, rough; veins prominent on lower surface. Color: Developing and fully expanded foliage, upper surface: Close to 147A; venation, close to 147B. Developing and fully expanded foliage, lower surface: Close to 147B; venation, close to 147B to 147C. Petiole: Length: About 5 mm to 20 mm. Diameter: About 3 mm. Texture, upper and lower surfaces: Pubescent. Color, upper and lower surfaces: Close to 147B.

Inflorescence description:

*Appearance.*—Decorative anemone-type inflorescence form with elliptic-shaped ray florets and enlarged disc florets. Inflorescences borne on terminals, arising from leaf axils. Ray and disc florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about seven weeks later when grown as a natural spray.

*Postproduction longevity.*—In an interior environment, inflorescences and foliage will maintain good color and substance for about three weeks.

*Quantity of inflorescences.*—Freely flowering habit, about 20 inflorescences per flowering stem develop.

*Spray width.*—About 15 cm.

*Inflorescence size.*—Diameter: About 6 cm to 7 cm. Depth (height): About 2 cm. Disc diameter: About 2 cm.

*Inflorescence buds.*—Shape: Oblate. Height: About 5 mm. Diameter: About 8 mm to 10 mm. Color: Close to 137B.

*Ray florets.*—Length: About 2 cm to 3.5 cm. Width: About 9 mm to 14 mm. Shape: Elliptic. Aspect: Concave. Apex: Broadly acuminate. Base: Attenuate. Margin: Entire. Texture: Smooth, glabrous; longitudinally ridged. Number of ray florets per inflorescence: About 45 arranged in numerous rows. Color: When opening, upper surface: Close to 2D. When opening, lower surface: Close to 4D. Fully opened, upper surface: Close to 4C. Fully opened, lower surface: Close to 2D.

*Disc florets.*—Shape: Tubular, enlarged. Length: About 6 mm to 18 mm. Diameter: About 1 mm to 4 mm. Number of disc florets per inflorescence: About 100. Color: Immature: Close to 145B. Mature: Towards the apex, close to 5A; mid-section, close to 4B; towards the base, close to 145C to 145D.

*Phyllaries.*—Shape: Deltoid. Apex: Acute. Base: Truncate. Margin: Entire. Texture, upper surface: Smooth, glabrous. Texture, lower surface: Slightly pubescent. Color, upper surface: Close to 146A. Color, lower surface: Close to 147A to 147B.

*Peduncles.*—Length, first peduncle: About 4 cm. Length, fourth peduncle: About 8 cm. Diameter: About 2 mm to 3 mm. Angle: About 45° from vertical. Strength: Strong. Texture: Pubescent; longitudinally ridged. Color: Close to 137C.

*Reproductive organs.*—Androecium: Not observed. Gynoecium: Present on both ray and disc florets. Stigma length: About 5 mm. Stigma width: About 3 mm. Stigma shape: Bi-parted. Stigma color: Close to 145B; towards the apex, close to 7A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Mona Lisa Yellow' as illustrated and described.

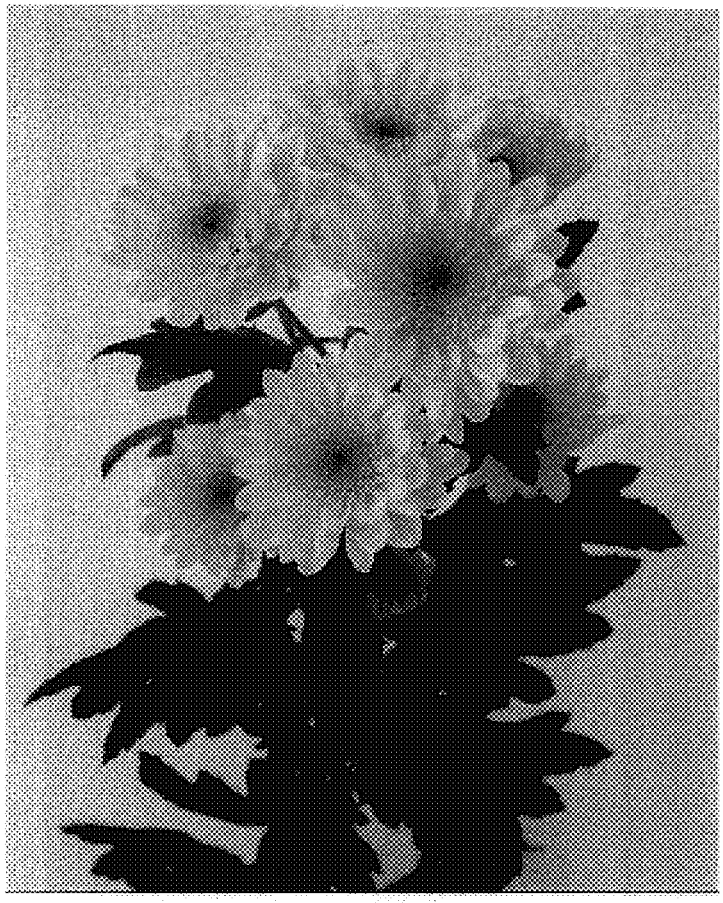
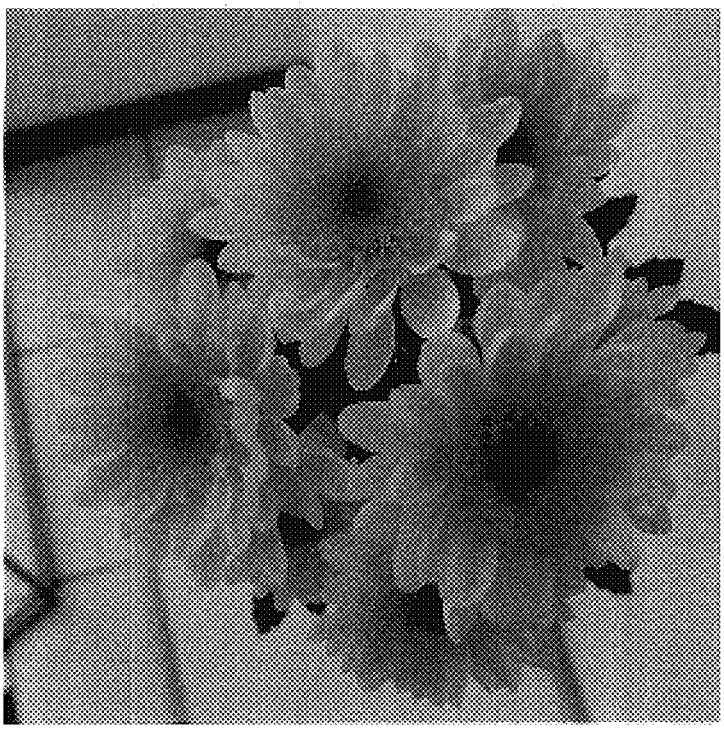

* * * * *